United States Patent
Warner et al.

(10) Patent No.: US 6,946,284 B2
(45) Date of Patent: Sep. 20, 2005

(54) SOLUBILIZING CROSS-LINKED POLYMERS WITH PHOTOLYASE

(75) Inventors: John C. Warner, Quincy, MA (US); Alessandra Morelli, Edinburgh (GB); Man Ching Ku, Boston, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/295,729

(22) Filed: Nov. 15, 2002

(65) Prior Publication Data

US 2003/0224497 A1 Dec. 4, 2003

Related U.S. Application Data

(60) Provisional application No. 60/333,816, filed on Nov. 16, 2001.

(51) Int. Cl.[7] .............................. B09B 3/00; C12P 1/00
(52) U.S. Cl. ..................... 435/262.5; 435/41; 435/262
(58) Field of Search ..................... 435/41, 262, 262.5; 424/486

(56) References Cited

U.S. PATENT DOCUMENTS 5,455,349 A * 10/1995 Grasshoff et al. ........... 544/309
5,616,451 A      4/1997 Grasshoff et al.
5,708,106 A      1/1998 Grasshoff et al.

OTHER PUBLICATIONS

Schultz, "Catalytic Antibodies", Acc. Chem. Res., vol. 22, pp. 287–294, 1989.

Cochran et al., "Photosensitized Cleavage of a Thymine Dimer by an Antibody", J. Am. Chem., vol. 110, pp. 7888–7890, 1988.

Moghaddam et al., "Photolysis of Polyamides Containing Thymine Photodimer Units in the Main Chain and Application to Deep–UV Positive Type Photoresists", *Polymer Journal* 22(6): 468–476 (1990).

* cited by examiner

*Primary Examiner*—David M. Naff
*Assistant Examiner*—Deborah K. Ware
(74) *Attorney, Agent, or Firm*—Fish & Richardson P.C.

(57) ABSTRACT

The invention relates to methods of solubilizing and recycling polymers using irradiation, wherein the polymers comprise photoreactive moieties. These polymers have many applications including use in disposable consumer products such as beverage bottles, eating utensils and diapers.

20 Claims, No Drawings

SOLUBILIZING CROSS-LINKED POLYMERS WITH PHOTOLYASE

CROSS-REFERERENCE TO RELATED APPLICATION

This application claims priority from U.S. Provisional Patent Application Ser. No. 60/333,816, filed on Nov. 16, 2001, which is incorporated herein by reference in its entirety.

TECHNICAL FIELD

The invention relates to methods of reprocessing polymers.

BACKGROUND

Polymers have broad commercial applications ranging from use in consumer products such as diapers and beverage bottles, to industrial applications such as photoresists, stencils, and films. Typical polymers are made from organic solvent-dependent monomers that undergo polymerization upon irradiation. These often-toxic monomers are recollected in a step that involves an organic wash and therefore requires strict monitoring of waste and solvent evaporation.

Although many polymers are insoluble in water, thymine polymers are generally water-soluble, unless treated. For example, one can cross-link the thymine moieties in the polymer chains to cause the polymer to become insoluble. This cross-linking can be accomplished, for example, by irradiating the polymer at the proper wavelength. The irradiation causes the thymine moieties to undergo a [2+2] photoreaction (a cyclization between two thymine moieties), which connects them to form four-membered rings. The cross-linking causes the polymers to become insoluble and stable to various environmental conditions. The physical characteristics of theses polymers can be controlled by the quantity of the thymine moieties used as co-monomers in the synthesis of the polymer. Once crosslinked, these thymine polymers are fairly resilient.

SUMMARY

The invention is based on the discovery that irradiation of [2+2] photo cross-linked polymers in the presence of the proper enzymes, such as DNA photolyase, reverses the cross-linking and causes the polymers to become water-soluble, provided the polymers were originally water-soluble prior to cross-linking. Prior methods of degrading these cross-linked polymers, such as photo-dissociation, have required harsh conditions. Additionally, these methods resulted in dissociation of the polymer chain itself as opposed to the selective reaction with the photolyase of only reversing the [2+2] cross-links by reversing the formation of the four membered rings.

In general, the invention features a method of solubilizing a cross-linked polymer. The method includes obtaining a cross-linked polymer, wherein the cross-links are formed by [2+2] cyclization reactions between photoreactive moieties of the polymer. The polymer is then contacted with an enzyme that recognizes [2+2] cyclization products, forming a polymer-enzyme mixture. The mixture is then irradiated for a time sufficient to solubilize the polymer. In these methods, the photoreactive moieties can be thymine or uracil and can be present in the polymer at from 3%–50% by weight. The polymer can be irradiated with broad UV light, UV light at specific wavelengths, such as 285 nm, or visible light. The enzyme can be DNA photolyase.

In another embodiment, the invention features products made of cross-linked polymers, wherein the cross-links are formed by [2+2] reactions between photoreactive moieties of the polymer. The polymers can be solubilized using enzymes that recognize [2+2] reaction products. Examples of products include beverage bottles, eating utensils, dishes, bags, or diapers, i.e., any product typically made of polymers and that are desirably recycled.

The invention also features a method of recycling a polymer. The method includes obtaining a water-soluble polymer made from photoreactive moieties capable of participating in [2+2] cross-linking reactions. The water-soluble polymer is then irradiated for a time sufficient to cross-link the polymer, making the polymer water-insoluble. In this way, the polymer can be used in a variety of products including beverages bottles and infant diapers. The cross-linked polymer is contacted with an enzyme that recognizes [2+2] cyclization products, forming a polymer-enzyme mixture. Then, the polymer-enzyme mixture is irradiated for a time sufficient to render the polymer water-soluble. The polymer can be irradiated with UV light, e.g., at a wavelength of 285 nm, to become water-insoluble.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

The new methods of degrading [2+2] cross-linked polymers achieve the goal of creating a polymer that is robust and resistant to water and exposure to air and sunlight until a time when it is to be recycled, at which point it can easily be made water-soluble and biodegradable. Under both economical and environmentally friendly conditions, the polymer can be selectively degraded and subsequently either removed with water, recycled into a new product, or both.

The details of one or more embodiments of the invention are set forth in the accompanying drawings and the description below. Other features, objects, and advantages of the invention will be apparent from the description and drawings, and from the claims.

DETAILED DESCRIPTION

Typical plastic materials are made from organic solvent-dependent, water-insoluble monomers that undergo polymerization upon irradiation. Thymine-based polymers, on the other hand, can be water-soluble. However, these polymers can undergo a photoreaction, initiating a cross-linking mechanism, where neighboring polymer strands are "tied" together. This formation of cross-links makes the polymers water-insoluble and able to withstand a variety of environmental conditions. These characteristics are required for a number of useful applications of these polymers.

Reversal of the cross-links causes the polymers to again become water-soluble. The invention provides simple and economical methods to achieve reprocessing of these polymers, thus making them easily recyclable. Irradiation of these cross-linked polymers in the presence of certain enzymes, such as DNA photolyase effectively reverses the photocross-linking in an efficient manner under mild conditions. Creating more environmentally friendly polymer products is a goal of many corporations and research institutions. The new methods make considerable progress in reaching this goal.

General Methodology

In one embodiment, the invention provides a method of recycling a polymer. A water-soluble polymer incorporating photoreactive moieties capable of participating in [2+2] cyclization reactions is synthesized using methods known in the art. Examples of the photoreactive moieties include thymine (e.g., benzyl thymine), uracil, and other organic molecules capable of participating in [2+2] cyclization reactions in polymer chains. The photoreactive moieties of the polymer comprise about 3%–50% by weight of the polymer, e.g., 4, 5, 7, 10, 12, 15, 20, 25, 30, 35, 40, or 45% by weight.

Such polymers can include multi-functional vinylbenzyl and vinylphenyl pendant thymine (and/or uracil) groups, and are described, for example, in U.S. Pat. Nos. 5,708,106 and 5,455,349. Such monomers, and polymers made from such monomers, are commercially available. The water-soluble polymer is then irradiated for a time sufficient to cross-link the polymer. Broad UV light or actinic radiation, e.g., UV light at specific wavelengths, such as 285 nm, can be used to cause cross-linking of the polymer. Irradiation of the polymer initiates the [2+2] cyclization reaction between the photoreactive moieties, which causes the polymer to become insoluble as well as to become stable to other environmental conditions (e.g., air and light).

The water-insoluble, cross-linked polymer is then contacted with an enzyme that recognizes [2+2] cyclization products, forming an enzyme-polymer mixture. The enzyme is a photolyase, such as DNA and other photolyases from various bacteria (such as $E.\ coli$, in which DNA photolyase is encoded by the phr gene) and other organisms (e.g., fish and frogs). Only catalytic amounts of the enzyme are required (e.g., 0.1% to 1% by weight). The resulting polymer-enzyme mixture is irradiated, e.g., with UV or actinic radiation, for a time sufficient to solubilize the polymer (e.g., less than 5 minutes). The enzyme can be recycled and used over and over again (e.g., by repeating the methodology described above), adding to the economic and environmental advantages.

In another embodiment, the invention provides methods of solubilizing polymers. A polymer that is cross-linked through [2+2] cyclization reactions between photoreactive moieties of the polymer chain is contacted with an enzyme that recognizes [2+2] cyclization products, forming a polymer-enzyme mixture. The resulting polymer-enzyme mixture is then irradiated (treated with a sufficient amount of radiation) under conditions sufficient to solubilize the polymer.

In another embodiment, the invention is a product comprised of a polymer cross-linked through [2+2] cyclization reactions, capable of being solubilized using an enzyme that recognizes [2+2] reaction products.

Applications

Consumers consistently choose products that are disposable. While these products are popular because they are convenient, they often end up in landfills, causing harm to the environment. Although there has recently been an increased awareness of the importance of preserving our land resources, disposable consumer products remain popular due to their low cost and their convenience. Polymers have a broad array of applications and are used in the manufacture of many disposable consumer products.

The new economic and environmentally friendly methods of recycling polymeric products will have a significant positive impact on the environment. These new methods provide a means of reducing the number of consumer products that are currently disposed in landfills. In addition, they will reduce the air and water pollution involved in recycling traditional polymers by providing a non-toxic recycling method that does not require organic solvents or harsh conditions. All that is needed in the new recycling method is a source of irradiation, water, and a catalytic amount of an enzyme, which itself can be recycled and reused repeatedly. These advantages provide producers of consumer products a viable, more environmentally friendly alternative to manufacturing and recycling than what is currently available, without increasing cost to consumers or sacrificing convenience of the products.

Examples of products that can by recycled using the new method include beverage bottles, dishes, eating utensils, bags, and diapers, and any other products, such as consumer products, made of polymers. For these products, the polymers described herein can include various additives, such as colorants or pigments, fillers, and other additives, as long as they do not interfere with the new methods.

EXAMPLES

The invention is further described in the following examples, which do not limit the scope of the invention described in the claims.

Example 1

Formation and Solubilization of a Polymer Product

A copolymer of 1-[4-vinylbenzyl]thymine and [4-vinylbenzyl]trimethylammonium chloride in a 1:4 ratio was synthesized using free radical polymerization. The polymer was dissolved in water to form a 10% solution and cast on a polyethylene terphtalate ("PET") support with a #3 gauge coating rod. Regions of the polymer film were selectively exposed to broad UV light for 50 seconds, thereby cross-linking the exposed regions. The film was washed with water, and the non-irradiated, still soluble, polymer was removed. The regions where the polymer was irradiated with UV light became insoluble and remained on the support.

Some samples of the residual polymer were visualized by toning with an anionic dye to verify crosslinking.

DNA photolyase and reaction buffer solution (PharMingen Int., Becton Corp.) were applied to regions by covering a portion of the previously exposed films with a small volume of an enzyme solution by spraying. Control regions were treated with water by soaking in a solution not containing the enzyme.

The polymer in the regions of the films that had the DNA photolyase applied was solubilized and removed by the process. No effect was seen in the controls.

The residual polymer was visualized by toning with an anionic dye.

Example 2

Recycling of a Polymeric Beverage Container

An appropriately clean bottle, made from an organic polymer containing cross-linked photoreactive moieties, is placed in a vat containing an aqueous solution of DNA photolyase (PharMingen Int., Becton Corp.). The entire vat is irradiated with broad UV light for a time sufficient to reverse the cross-linking of the organic polymer. The enzyme-containing solution is then separated from the polymer mixture. The remaining polymer mixture is dried and used in a mold or dye, forming a new polymer product. Alternatively, the polymer mixture can be used without evaporation of the solvent, and directly applied to a dye, mold, or cast.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of solubilizing a polymer, the method comprising;
   (a) obtaining a cross-linked polymer, wherein cross-links in the cross-linked polymer are formed through [2+2] cyclization reactions between photoreactive moieties of neighboring polymer strands of a soluble polymer;
   (b) contacting the cross-linked polymer with at least a catalytic amount of a photolyase that recognizes [2+2] cyclization cross-links to form a polymer photolyase mixture; and
   (c) irradiating the polymer photolyase mixture for a time sufficient to break the cross-links in the cross-linked polymer to solubilize the cross-linked polymer.

2. The method of claim 1, wherein the photoreactive moieties are thymine.

3. The method of claim 1, wherein the photoreactive moieties are benzyl thymine.

4. The method of claim 1, wherein the photoreactive moieties are uracil.

5. The method of claim 1, wherein the photoreactive moieties of the soluble polymer comprise about 3%–50% by weight of the soluble polymer.

6. The method of claim 1, wherein the soluble polymer comprises segments derived from a vinylbenzyl thymine monomer.

7. The method of claim 1, wherein the cross-linked polymer is irradiated with UV light.

8. The method of claim 1, wherein the cross-linked polymer is irradiated with UV light at 285 nm.

9. The method of claim 1, wherein the cross-linked polymer is irradiated with visible light.

10. The method of claim 1, wherein the photolyase is a DNA photolyase.

11. The method of claim 1, wherein the cross-linked polymer by itself or together with one or more other polymers forms at least a part of a product selected from the group consisting of a bottle, eating utensil, dish, bag, and diaper.

12. The method of claim 11, wherein the product is a bottle.

13. The method of claim 11, wherein the product is a diaper.

14. The method of claim 11, wherein the product includes an additive.

15. The method of claim 14, wherein the additive is a colorant or a pigment.

16. The method of claim 1, wherein the solubilized polymer is processed by itself or together with one or more other polymers to form at least a part of a product selected from the group consisting of a bottle, eating utensil, dish, bag, and diaper.

17. The method of claim 16, wherein the product is a beverage bottle.

18. The method of claim 16, wherein the product is an eating utensil.

19. The method of claim 16, wherein the product is a bag.

20. The method of claim 16, wherein the product is a diaper.

* * * * *